United States Patent [19]

Gerow

[11] Patent Number: 4,957,487
[45] Date of Patent: Sep. 18, 1990

[54] EXTERNAL MALE URINARY CATHETER AND COLLECTION SYSTEM

[75] Inventor: Frank J. Gerow, Houston, Tex.

[73] Assignee: Baylor College of Medicine, Houston, Tex.

[21] Appl. No.: 292,559

[22] Filed: Dec. 30, 1988

[51] Int. Cl.⁵ .................................................. A61M 37/00
[52] U.S. Cl. .................................................. 604/133
[58] Field of Search ................................. 4/144.1–144.4; 604/133, 134, 347, 349–353

[56] References Cited

U.S. PATENT DOCUMENTS

| | | | |
|---|---|---|---|
| 882,092 | 5/1906 | Woodruff . | |
| 2,389,831 | 11/1945 | Welsh | 2/21 |
| 2,789,560 | 4/1957 | Weimer | 128/295 |
| 2,940,450 | 6/1960 | Witt et al. | 128/295 |
| 2,947,470 | 8/1960 | Ruben et al. | 230/160 |
| 3,032,038 | 5/1962 | Swinn | 128/295 |
| 3,058,627 | 10/1962 | Eskridge | 222/210 |
| 3,112,061 | 11/1963 | Breer | 230/79 |
| 3,115,138 | 12/1963 | McElvenny et al. | 128/278 |
| 3,161,197 | 12/1964 | Glas et al. | 128/295 |
| 3,201,111 | 8/1965 | Afton | 267/1 |
| 3,339,551 | 9/1967 | Stoutenburgh | 128/295 |
| 3,349,768 | 10/1967 | Keane | 128/276 |
| 3,353,538 | 11/1967 | Carrigan | 128/295 |
| 3,421,504 | 1/1969 | Gibbons | 128/278 |
| 3,511,241 | 5/1970 | Lee | 128/295 |
| 3,559,651 | 2/1971 | Moss | 128/295 |
| 3,608,552 | 9/1971 | Broerman | 128/295 |
| 3,631,857 | 1/1972 | Maddison . | |
| 3,661,156 | 5/1972 | McLaughlin | 128/295 |
| 3,739,783 | 6/1973 | Broerman | 128/295 |
| 3,835,857 | 9/1974 | Rogers et al. | 128/295 |
| 4,175,554 | 11/1979 | Gerow | 128/79 |
| 4,239,044 | 12/1980 | Pavlinch | 128/295 |
| 4,284,079 | 8/1981 | Adair | 128/295 |
| 4,312,350 | 1/1982 | Doan | 128/276 |
| 4,345,342 | 8/1982 | Saito | 4/301 |
| 4,366,818 | 1/1983 | Izumi | 128/295 |
| 4,387,726 | 6/1983 | Denard | 604/349 |
| 4,443,217 | 4/1984 | Izumi | 604/73 |
| 4,475,909 | 10/1984 | Eisenberg | 604/349 |
| 4,475,910 | 10/1984 | Conway et al. | 604/352 |
| 4,484,918 | 11/1984 | Omley | 604/349 |
| 4,500,314 | 2/1985 | Brendling | 604/346 |
| 4,529,402 | 7/1985 | Weilbacher | 604/133 |
| 4,540,409 | 9/1985 | Nystrom et al. | 604/349 |
| 4,553,968 | 11/1985 | Komis | 604/349 |
| 4,559,049 | 12/1985 | Haan | 604/350 |
| 4,573,985 | 3/1986 | Finny | 604/349 |
| 4,588,397 | 5/1986 | Gracolone | 604/349 |
| 4,589,874 | 5/1986 | Riedel et al. | 604/349 |
| 4,690,135 | 9/1987 | Gerow | 128/79 |
| 4,713,066 | 12/1987 | Komis | 604/353 |

Primary Examiner—David J. Isabella
Attorney, Agent, or Firm—Fulbright & Jaworski

[57] ABSTRACT

An external male urinary catheter and collection system utilizes a sheath-like member for accepting the male penis, a negative pressure evacuation device communicating with the sheath-like member, the negative pressure causing the penis to elongate in a simulated erection, and a thin-walled sealing portion of the sheath-like member to provide an air-tight seal about the elongated penis. A one-way drainage tube to permit draining of urine into the evacuation device and a one-way air tube to permit equalization of the negative pressure between the sheath-like member and the evacuation device after urine has been voided into the evacuation device are also provided. The evacuation device may be worn attached to the leg of the wearer.

34 Claims, 4 Drawing Sheets

EXTERNAL MALE URINARY CATHETER AND COLLECTION SYSTEM

BACKGROUND OF THE INVENTION

The present invention relates to an external urinary catheter and collection system for use by an incontinent male. More specifically, the present invention relates to an external male urinary catheter and collection system that utilizes a negative pressure for retaining the sleeve-like catheter on the male penis and for collecting urine passed by the wearer.

A recent survey estimates that there are approximately 35 million incontinent adults in the United States. Of that number, approximately one-third are male and two-thirds are female. Most of the incontinent males are elderly, or have bladder or urinary tract diseases or may be spinal cord victims that have lost control of certain bodily functions. Incontinence is a physical problem that has severe psychological effects because of the fear of the incontinent person that an "incontinence accident" will occur in public with corresponding embarrassment and shame. Many incontinent persons refuse to go out in public and lead private reclusive lives because of the fear and stigma associated with a public "incontinence accident".

Many attempts have been made to overcome this problem, originally, by use of a catheter (classical medical definition) inserted into the urinary tract of the patient. However, long-term invasive catheter insertion almost universally leads to repeated urinary tract and bladder infections with the resulting need for treatment and removal of the catheter while the infection is treated. Such continuing infections also have a negative impact on the general health of the patient.

The "internally" inserted catheter referred to above is the type meeting the "classic" medical definition of a "catheter", as typically defined in *Webster's Medical Desk Dictionary* (Merriam Webster, Inc., 1986) as "a tubular medical device for insertion into canals, vessels, passageways, or body cavities usually to permit injection or withdrawal of fluids or to keep a passage open." Attempts at developing "external" catheters (non-invasive) for male patients have been tried, in which the "external" catheter is attached externally to the male penis and does not invade the urethra. The earliest and simplest of such "external catheter" utilizes a rubber, sleeve-like device similar to a condom that has a rubber tube attached to its distal end for drainage of urine. Other attempts have utilized various sheath-like devices for attachment to the male penis with drainage tubes and bags for collecting the urine.

A major problem has been encountered in attaching the apparatus to the male penis. A condom-like device will not stay attached to a male penis in a flaccid state unless some type of adhesive or tape is utilized. Prolonged use of an adhesive or tape causes skin rashes and irritations on the contacted skin of the penis. Such irritations often become painful and infected, thus limiting the use of the device. Some devices use a harness about the hips of the wearer for supporting the device on the penis, or an undergarment to which a sheath-like device is attached. However, the problem of maintaining a flaccid penis in the sheath-like portion of such devices persists.

Another problem associated with many of such prior art "external" catheters is that after voiding some urine often remains in the penile sheath in contact with the skin of the penis. Prolonged contact of urine and the penile skin also causes skin rashes and irritations that are painful and may lead to skin and urinary tract infections. No effective means of overcoming such a problem has been found for ambulatory males with an incontinence problem that will permit them a range of normal movement and activities.

Accordingly, one primary feature of the present invention is to provide an external male urinary catheter and collection system that is easy to attach, comfortable to wear and may be worn for extended periods of time without danger of irritation to the skin of the male penis.

Another primary feature of the present invention is to provide a sheath-like member for attachment to the male penis that is maintained in place by means of negative pressure without the need of adhesive or tape.

Still another feature of the present invention is to provide a negative pressure evacuation device communicating with the sheath-like member that will effect a negative pressure therein for causing the male penis to elongate in a simulated erection and provide sufficient surface area for effecting an airtight seal with the sheath-like member.

Another feature of the present invention is to provide a one-way urine drainage tube communicating between the sheath-like member and a negative-pressure evacuation device for permitting urine flow from the sheath-like member to the evacuation device for collection.

Still another feature of the present invention is to provide a one-way air pressure equalization tube communicating between a negative-pressure evacuation device and the sheath-like member for permitting equalization of the negative air pressure therebetween.

BRIEF SUMMARY OF THE INVENTION

The present invention remedies the problems of the prior art by providing an external male urinary catheter and collection system that utilizes a sheath-like member for accepting the male penis and a negative pressure evacuation device communicating with the sheath-like member, the negative pressure causing the penis to elongate in a simulated erection within the sheath-like member for permitting a thin-walled sealing portion thereof to provide an air-tight seal about the elongated penis. The catheter also includes a drainage tube to permit drainage of urine from the sheath-like member to the evacuation device and an air pressure equalization tube to permit equalization of the negative pressure between the sheath-like member and the evacuation device after urine has been voided into the evacuation device.

In accordance with a principle of this invention, apparatus for providing an external male urinary catheter and collection system is provided that includes a generally cylindrical, flexible, hollow body member having a distal closed end and a proximal open end for accommodating the male penis interiorly thereof, and a flexible, thin-walled, sleeve-like sealing member integrally extending from the proximal open end of the body member and in concentric axial alignment therewith. The apparatus further includes a first flexible tube one end of which is connected to the distal end of the body member and communicating with the interior thereof for permitting drainage of urine, a first one-way valve cooperating with the other end of the drainage tube to permit one-way urine flow from the interior of the body member, a second flexible tube one end of which is connected to the distal end of the body member adjacent the first flexible tube and communicating with the interior of the body member, and a second one-way valve cooperating with the second flexible tube to permit one-way air flow therethrough into the interior of the body member.

In addition, the invention also includes a pair of clamps cooperating externally with each of said first and second flexible tubes for selectively clamping the tubes for prohibiting fluid and/or air flow therethrough. An evacuation device is interconnected to the other ends of the first and second flexible tubes for introducing a negative pressure into the body member interior through the first flexible tube when the clamp is opened and permitting evacuation and collection of urine from the body member through the first flexible tube into the evacuation device. The evacuation device may be adapted for ambulatory use by a strap that attaches the device to the wearer's leg.

The sleeve-like sealing member has a flexible thin-wall for permitting the sealing member to be rolled up over the adjacent portion of the body member to permit the insertion of the distal end of the male penis into the proximal end of the body member and then allowing the thin-walled sleeve-like sealing member to be returned to its unrolled extended position in circumferential contact with the exterior of the penile shaft. The evacuation device introduces a negative pressure into the body member interior which acts on the non-erect penile shaft for drawing the penis into the interior of the body member to or near to its anatomical limit, and further acting on the thin-walled sleeve-like sealing member for collapsing the thin walls circumferentially about the penile shaft for maintaining an air-tight seal therewith. The negative pressure introduced into the interior of the body member by the evacuation device further aids in the drainage of urine from the body member through the first flexible tube and one-way valve into the evacuation device for collection.

After the clamp on the second tube is opened, the second flexible tube and second one-way valve cooperate with the evacuation device and the interior of the body member for permitting a reverse flow of a volume of air therethrough from the evacuation device into the interior of the body member for substantially equalizing the negative pressure between the interior of the body member and the evacuation device and displacing sufficient urine collected in the first tube into the evacuation device for clearing urine from the interior distal end of the body member. The volume of such reverse flow of air from the evacuation device to the interior of the body member is functionally related to the volume of air displaced by the urine flow into the evacuation device.

BRIEF DESCRIPTION OF THE DRAWINGS

In order that the manner in which the above-recited advantages and features of the invention are attained can be understood in detail, a more particular description of the invention may be had by reference to specific embodiments thereof which are illustrated in the accompanying drawings, which drawings form a part of this specification.

In the drawings.

DETAILED DESCRIPTION OF THE INVENTION

Figure 1:
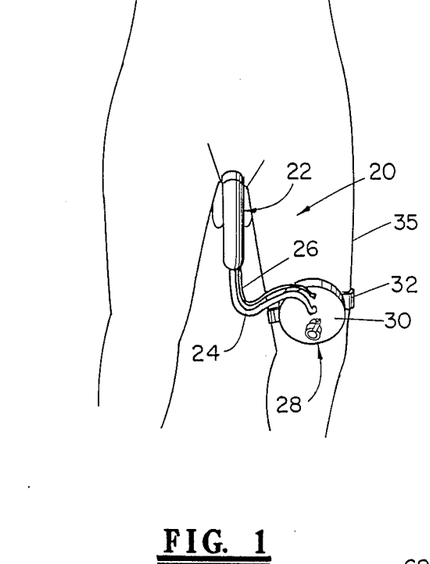
FIG. 1 is a perspective view of the present invention illustrating the application of the external catheter to the male penis and attachment of the cooperating evacuation device to the male patient's leg.

In the description that follows, the terms "external male urinary catheter" or "external male catheter" shall mean the "non-invasive" type of device attached externally to a male penis as hereinbefore defined and as contrasted to the classic medical definition of an "invasive" device. Referring now to FIG. 1, one embodiment of the external male urinary catheter and collection system 20 is shown being worn by an incontinent male, and comprises a sheath-like member 22 attached to the male penis (the attachment details of which will be hereinafter described in greater detail), an evacuation device 28 having a top surface 30, and a pair of tubes 24 and 26 interconnecting the sheath member 22 and the evacuation device 28 through its top 30. The evacuation device 28 may be removably attached to the wearer's leg 35 by means of a strap 32. The tubing 24 is a drainage tube for urine, while the tube 26 is an air-pressure equalization tube as will hereinafter be further described. The evacuation device 28, when activated, produces a negative air-pressure within the system 20 and acts as a collection receptacle for urine which drains into the interior of device 28 through the drainage tube 24.

Figure 2:
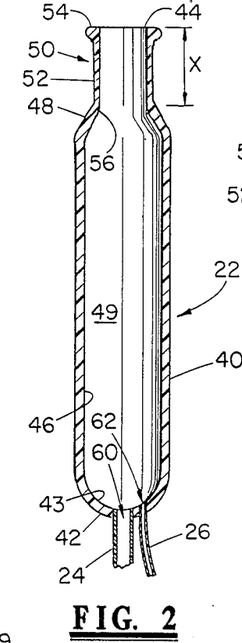
FIG. 2 is a vertical cross-sectional view of the sheath-like member for attachment to the male penis.

FIG. 2 shows the details of the sheath-like member 22 which comprises a generally penile-shaped, sleeve-like, smooth walled, relatively soft and pliable hollow cylindrical or tubular body member 40 with a closed external distal end 42 and an opposed open end 44. A smooth inner wall surface 46 defines an interior chamber 49 having a predetermined substantially constant circumferential measurement extending from the inner distal end 43 to the interior shoulder 56. A sleeve-like sealing member 50 includes a thin-walled section 52 integrally extending from shoulder 48 to the proximal open end 44 (length "X") and terminates in an edge bead 54. The body member 40 has a relatively thicker wall section than does the sealing member 50.

The sealing member 50 includes a thin-walled, flexible, sleeve-like sealing portion 52 that has a substantially constant inner diameter that is less than the inner diameter of body member 40, and has a predetermined substantially constant inner circumferential measurement that is less than the general inner circumferential measurement of body member 40. The bead 54 is provided on the open end 44 of the sleeve-like sealing portion 52 to add additional strength to the open end 44 and to prevent tearing. The shoulder 48 provides a flexible transition portion interconnecting the adjacent open ends of the sleeve-like sealing member 52 and the body member 40. The shoulder or transition portion 48 positions the sleeve-like sealing section 52 in a concentric axial alignment with the elongated cylindrical body member 40.

The body member 40 and the thin-walled, sleeve-like sealing portion 52 are preferably constructed of a flexible plastic material such as a silicone rubber. The thin-walled, sleeve-like sealing portion 52 between bead 54 and the shoulder 48 may conveniently have a thickness ranging between 0.005 inches to 0.010 inches to form an extremely thin, flexible sealing section. It is important for the interior wall surface 46 of the body member 40 to be smooth and free of irregularities. Irregular or accordion-like wall surfaces will "mark" and/or "pinch" the penile shaft surface and increase the risk of long-term injury due to damage to the penile circulatory system. The wall thickness of body member 40 will be influenced by the rigidity of the material used in manufacturing the device. The more rigid the material, the thinner the wall thickness may be. Using a plastic resin material, such as a silicone rubber, having a durometer reading of 50, could conveniently have a wall thickness of 0.010 inches to 0.300 inches, for example.

The shoulder or transition section 48 provides a radiused inner shoulder 56 circumferentially disposed within the sheath 22 and axially intermediate the sleeve-like sealing member 52 and the body member 40. The shoulder 56 progresses from a thin-walled thickness integral with the sleeve-like sealing section 52 to the thicker wall section of the integral body member 40. Shoulder 56 also provides a smooth transition from the smaller inner diameter of the sleeve-like sealing portion 52 to the increased inner diameter of the body member 40.

Attached centrally of the body member distal end 42 is one end of a flexible tube 24 that communicates with the body member interior 49. Spaced closely adjacent to tube 24 is one end of a second tube 26 that is attached to the body member distal end 42 and also communicates with the interior 49 of the body member 40. The open ends of tubes 24 and 26 do not project interiorly past the inner distal surface 42 of the body member. Typically, tube 24 is of a larger diameter and thicker-walled than tube 26 and constitutes the urine drainage tube as previously described in FIG. 1. The tube 26 is generally of a much smaller diameter than drainage tube 24 and functions as the air-pressure equalization tube as described in FIG. 1.

Figure 3:
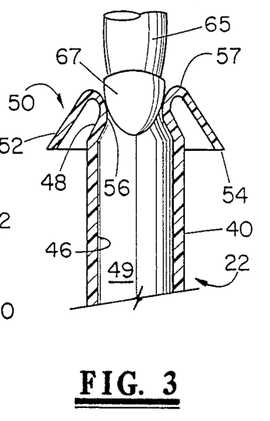
FIG. 3 is a partial vertical cross-sectional view of the sealing member of the device shown in FIG. 2, with the sleeve-like portion rolled back to facilitate insertion of the glans penis.
Figure 4:
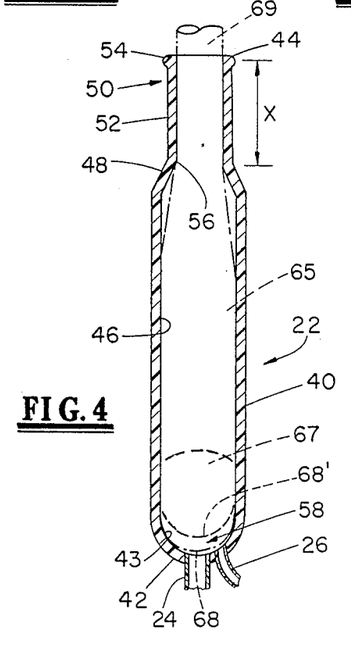
FIG. 4 is a vertical cross-section of the device shown in FIG. 2 with the penis fully drawn into the body member in simulation of an erection and showing the sealing member in place for providing an air-tight seal.
Figure 5:
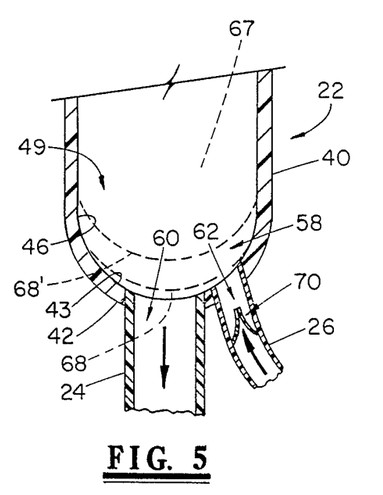
FIG. 5 is an enlarged partial vertical cross-sectional view of the distal end of the body member shown in FIG. 2 illustrating the interconnection of the drainage and air tubes thereto.

Referring now to FIGS. 3 through 5, the sealing member 52 is folded back over the transition or shoulder portion 48 unto the body member 40 as shown in FIG. 3. The glans penis 67, appropriately lubricated, is placed in the open rolled proximal end 57 of the sleeve-like sealing member 52 and engages the inner circumferential shoulder 56. Since the transition portion including shoulder 56 is flexible, the penis can be easily introduced therethrough and will react without appropriate negative pressure introduced to the interior 49 of the body member 40 as will be hereinafter described in greater detail. The negative pressure within the body member interior 49 will draw the flaccid penis 65 into the hollow interior 49 of the body member 40 and will continue to expand and lengthen the penis until it reaches its anatomic limit (or near anatomic limit) and occupies all or almost all of chamber 49 adjacent the distal end 42. If the body member is properly fitted, the end 68 of the glans penis 67 will fill the entire of the interior space 49 of the body member 40. However, on occasion the end 68 of the glans penis 67 may be spaced from the openings or entryways 60 and 62 into the drainage and air equalization tubes 24 and 26, respectively, and the most distal inner end 43 of the body member for providing a small space 58 therebetween.

The thin-walled sealing section 52 is rolled back to its original position so that the sealing member 50 now surrounds the proximal shaft portion 69 of the penis (see FIG. 4). This thin-walled sleeve-like sealing portion 52 functions as a valve, sealing the inside of the chamber 49 to the penis shaft 69. The sealing member 50, through its thin-walled portion 52, provides comfortable flexing of the penis 65 within the body member 40 without breaking the air-tight seal at 52 throughout the sealing section denominated as "X". Since the sealing section 52 has a thickness on the order of 0.005 inches to 0.010 inches, and is made of an extremely flexible, soft material, any turgescence of the penis 65 at the shaft portion 69 can be accommodated by the stretching of the sleeve-like sealing portion 52, thereby accommodating the wearer with a precise but comfortable fit.

The predetermined inner length measurement of body member chamber 49 is a function of the length of the penile shaft 65 in stretched non-erect condition, and is based on measurements provided by the user. The predetermined inner circumferential measurement of the sleeve-like sealing portion 52 is a function of the circumference of the penile shaft 69 adjacent to the penile shaft base in a stretched non-erect condition and is also based on measurements provided by the user. The radius of the outer surface of the shoulder 56 is selected to be sufficiently large enough not to injure the tissue of the erect penis 65 and to insure that the shoulder 56 does not restrict venous blood flow within the organ. The predetermined inner circumference of the sleeve-like sealing portion 52 of the sealing member 50 must be chosen to permit snug engagement with the penile shaft at 69 for functioning as a vacuum seal for the inner chamber 49 of the body member 40, but not engaging the penile shaft 69 tightly enough to restrict venous blood flow which could injure the penile tissue. The functions and advantages of such a smaller circumferential sealing member coaxially disposed with respect to the cylindrical axis of the body member 40 are disclosed in greater detail in U.S. Pat. No. 4,690,135.

In FIG. 5, an enlarged partial cross-sectional view of the distal end 42 of the body member 40 of the sheath-like device 22 is shown in greater detail. The end 68 of glans penis 67 is shown expanded either to engage the inner distal end surface 43 or to be in close proximity to the rounded surface of the inner distal end 43 of the body member 40, but having a potential space 58 therebetween as shown at 68'. As may be seen, urine will drain through the entryway 60 into the drainage tube 24 and into the evacuation device 28 (see FIG. 1). Air from the evacuation device 28, passing through the tubing 26, is allowed to flow only in one direction into the interior 49 of the body member 40 because of a one-way check valve 70. The valve 70 may conveniently be a thin membraned "duck bill" valve that will only open when there is a positive differential pressure across the valve in the direction of the arrow.

Figure 6:
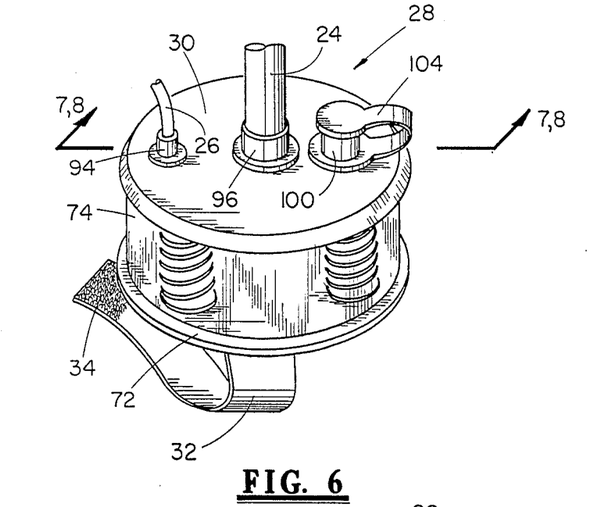
FIG. 6 is a perspective view of the evacuation device shown in FIG. 1.
Figure 7A:
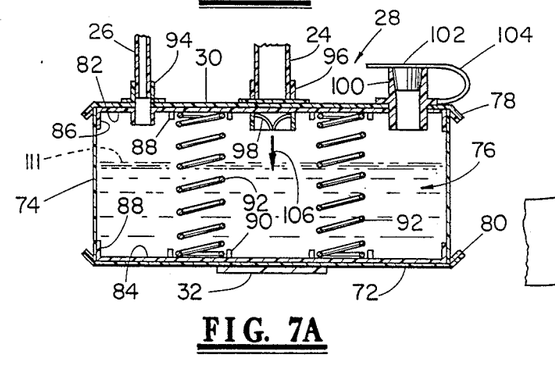
FIG. 7A is a vertical cross-sectional view of one embodiment of the evacuation device shown in FIG. 6, as taken approximately along the lines 7—7 of FIG. 6, showing the evacuation device in its fully expanded position.
Figure 7B:
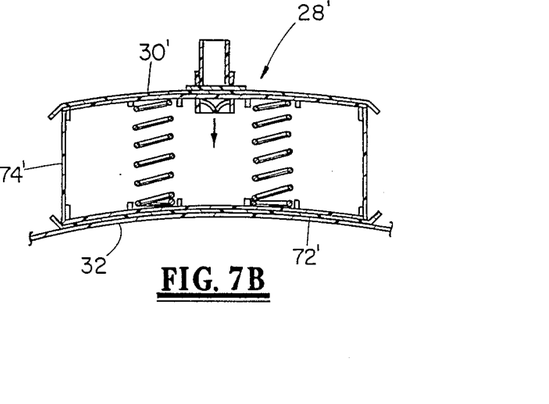
FIG. 7B is a vertical cross-sectional view of another embodiment of the evacuation device shown in FIG. 6, as taken approximately along the lines 7—7 of FIG. 6, showing an expanded evacuation device having at least one curved end wall.
Figure 8:
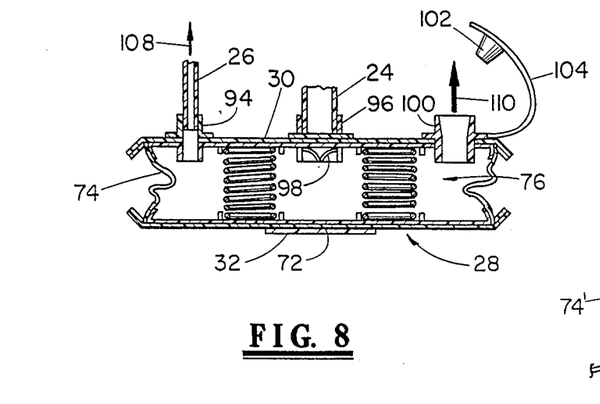
FIG. 8 is a vertical cross-sectional view of the evacuation device shown in FIG. 6, as taken approximately along the lines 8—8 of FIG. 6, showing the evacuation device in its fully compressed position for exerting a negative pressure on the interior of the body member.

Referring now to FIGS. 6–8, the structure and function of the evacuator device 28 will be described in greater detail. The evacuator device as utilized in this system, is similar in construction and function to the type described in U.S. Pat. No. 3,752,158, as manufactured by Snyder Laboratories, under the trademark HEMOVAC. However, the evacuator device 28, as described herein, while structurally similar, functions in connection with the penile sheath device 22 and tubing 26 to perform a function different than that generally provided by a standard evacuator device. Evacuator device 28 is a portable or ambulatory device that comprises opposed spaced annular-shaped end walls 30 and 72 that are joined by an annular connecting side wall 74 to define an interior chamber 76. The side and annular walls may be of a selected pliable plastic material and may be joined by annular seals at 78 and 80. The annular wall 74 may be transparent, and may include graduations (not shown) for indication of the volume of fluid therein.

Each of the end walls 30 and 72 is internally provided with a rigid backing member 82 and 84, having flanges 86 and 88 that are substantially adjacent to the wall 74 to enhance the rigidity of the backing members 82 and 84. Formed on the interior backing members 82 and 84 are inwardly projecting tubular spring retainers 88 and 90, there being a plurality on each backing member and axially aligned in pairs for retaining a plurality of springs 92. The springs 92 normally bias the backings 82 and 84 and their associated exterior side walls 30 and 72, respectively, to the normal expanded position shown in FIGS. 6 and 7A. Disposed in the exterior wall 30 are plastic nipples 94, 96 and 100 that are sealed to the wall 30. The nipple 100 integrally includes, attached to its edge, a short strap 104 that carries a removable closure plug 102 for insertion into the nipple 100 for closing and sealing it. For convenience, the side walls 30' and/or 72' may be curved to better fit and conform to the contour of the thigh of the user as shown in FIG. 7B.

The other end of the drainage tube 24, projecting from the body member 40, fits into and seals within the nipple 96 centrally of the evacuation device 28. Similarly, the air equalization tube 26 projecting from the body member 40, fits into and seals within the nipple 94 for communicating directly with the interior 76 of the evacuation device 28. Disposed within the lower portion of the flange 96 is a one-way check valve 98 for permitting fluid flow from the drainage tube 24 to flow only into the interior 76 of the evacuation device 28 as shown by the arrow 106 (see FIG. 7A). As shown in FIG. 8, with the plug 102 removed from nipple 100, the evacuation device 28 may be activated by applying pressure to the opposite side walls 30 and 72, and the air within the interior 76 is expelled through the exit port 100 in the direction shown by arrow 110. Air would also be expelled through tube 26 in the direction shown by arrow 108, unless the tube 26 is blocked as will be hereinafter described. The check valve 98 blocks the passage of air into the tubing 24.

Figure 9:
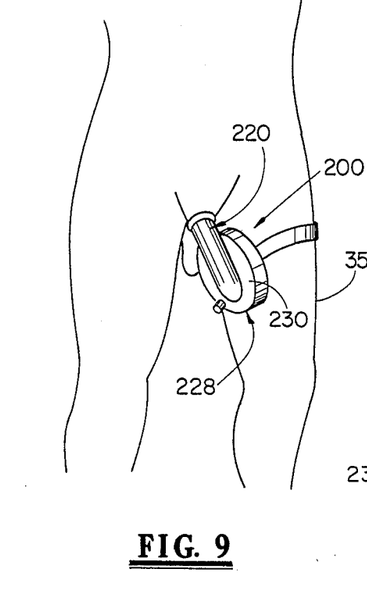
FIG. 9 is a perspective view of a second embodiment of the present invention illustrating the application of the external catheter and the cooperating evacuation device directly to the male penis and attachment of the evacuation device to male patient's leg.
Figure 13:
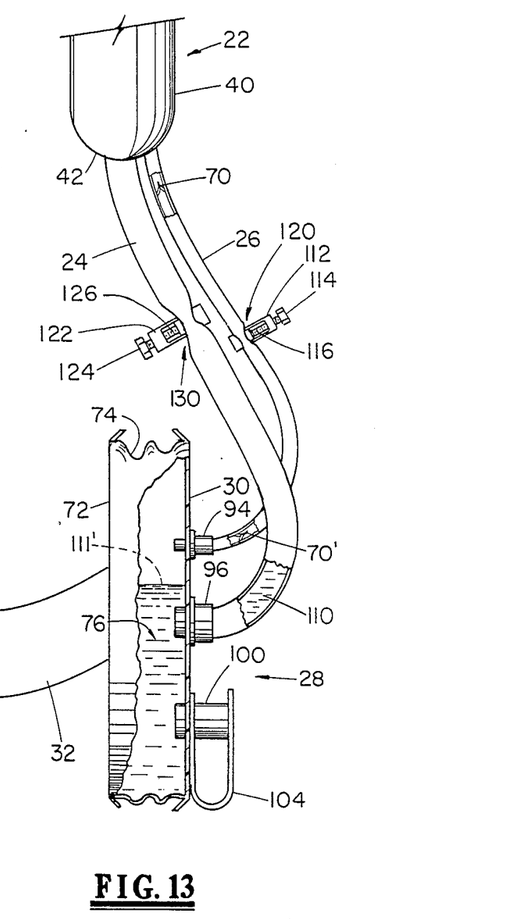
FIG. 13 is a perspective view of a portion of the external male urinary catheter and collection system with the evacuation device partially cut-away.

The evacuation device 28 may be utilized in a horizontal position as shown in FIGS. 6–8, if the patient or incontinent person is reclining in a horizontal position, for instance as in bed, or it may be oriented in a vertical position as shown in FIGS. 1 and 9, if the system 20 is being utilized as a portable device and worn on the thigh of the incontinent person. When the evacuation device 28 is oriented in a horizontal position as shown in FIGS. 7A or 7B, the urine collected through tubing 24 will drain into the lower half of the evacuation device 28 and fill the interior 76 of the device from the lower side wall 72 toward the upper side wall 30 as shown by the dotted line fluid level 111. In this way, the air equalization tube 26 and nipple 94 are always above the fluid level and communicating with the air space in the interior 76 of the device 28. However, as shown in FIG. 13, if the device 28 is oriented in a vertical position, the straps 32 orient device 28 such that the three flanges 94, 96 and 100 are oriented in a vertical row in descending order, respectively. Accordingly, urine collecting in the unit 28 through tube 24 will rise upwardly within the interior volume 76 to approach a maximum fluid level 111' below the entry of nipple 94 as shown in dotted lines. Therefore, the tubing 26 communicates through the nipple 94 into the device interior 76 above the fluid level.

FIGS. 9–12 illustrate a second embodiment of the external male urinary catheter and collection system 200 is shown. System 200 comprises a sheath-like member 220 attached to the male penis, and an evacuation device 228 having a top wall 230 that is attached to the sheath-like member 220 over substantially the longitudinal length of the member. The evacuation device 228 may be smaller in physical size and volume than the hereinabove described evacuation device 28. The previously described device 28 is sized to have a urine capacity of approximately 400 cc, and is primarily for incontinent persons who have little or no control over their bladder function. The second embodiment of the evacuation device 228 is sized for a urine capacity of approximately 200-300 cc and is primarily for those incontinent males who have basic bladder control, but who have occasional lapses of incontinence that could be embarrassing in public. The evacuation device 228 and attached sheath-like member 220 are conveniently pulled to one side and attached to the patient's thigh 35 by means of a strap 232. The sheath-like body member 220 is exactly of the same structure and function as the previously described body member 22, and therefore the previous description is incorporated herein for parallel reference numbers.

Figure 10:
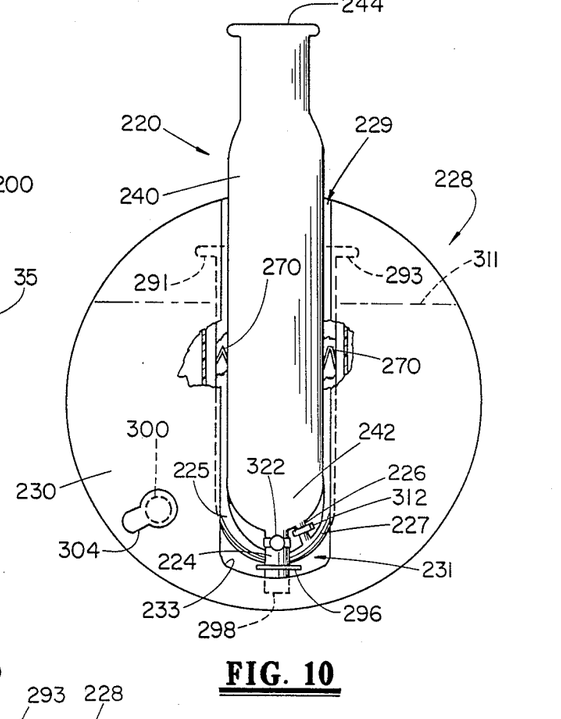
FIG. 10 is a top plan view of the evacuation device attached to the external catheter body member and male penis as shown in FIG. 9.
Figure 11A:
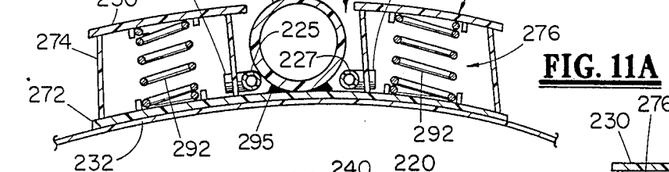
FIG. 11A is a vertical cross-sectional view of the second embodiment of the evacuation device shown in FIG. 10, as taken approximately along the lines of 11—11 of FIG. 10, showing the evacuation device in its fully expanded position.
Figure 12:
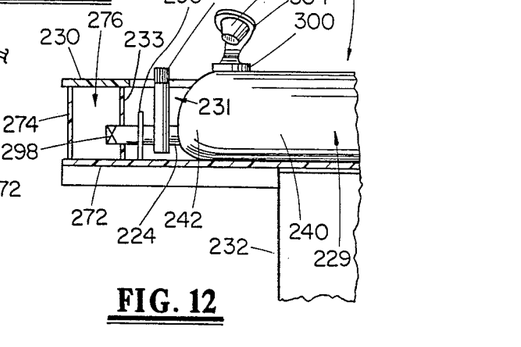
FIG. 12 is a fragmentary vertical cross-sectional view of the distal end of the penile sheath body member and the mounting of the urine drainage tube into the evacuation device.

Referring now to FIGS. 10 and 12, the construction and function of a second embodiment of the evacuator 228 will be described in greater detail. Evacuator device 228 comprises opposed spaced end walls 230 and 272 that are joined by an annular connecting side wall 274 to define an interior chamber 276. The end walls 230 and 272 may conveniently be cured for more comfortably fitting the patient's leg. In the embodiment shown, end wall 272 is preferably of a circular configuration while the top end wall 230 may be of a "U-shaped" configuration for defining an interior "U-shaped" space 229 to accommodate the longitudinal length of most of the sheath body member 240. The side and annular walls may be of a selected pliable plastic material and sealed to the end walls 230 and 276 in a similar fashion as in the construction of device 28. The annular wall 274 may be transparent, and may include graduations (not shown) for indication of the volume of fluid therein. A plurality of springs 292 normally bias the exterior side walls 230 and 272, respectively, to the normal expanded position shown in FIG. 11A. Disposed in the exterior wall 230 is plastic nipple 300 that is sealed to the wall 230. The nipple 300 integrally includes attached to its edge, a short strap 304 that carries a removable closure plug 302 (see FIGS. 10 and 12) for insertion into the nipple 300 for closing and sealing it in the same manner as the closure plug 102 and nipple 100 in the embodiment 28 of the evacuator device described above.

The elongated U-shaped opening 229 is sized and shaped to accommodate the distal end 242 and a portion of the cylindrical body member 240, which is attached to the upper surface of the lower end wall 272 by a suitable adhesive 295. A strap 232 is attached to the lower surface of the bottom end plate 272 for attachment of the evacuation device 228 and attached sheath-like member 220 to the patient's thigh as shown in FIG. 9.

Figure 11B:
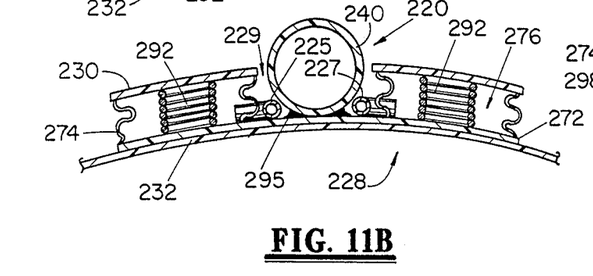
FIG. 11B is a vertical cross-sectional view of the second embodiment of the evacuation device shown in FIG. 10, as taken approximately along the lines 11—11 of FIG. 10, showing the evacuation device in its fully compressed position for exerting a negative pressure on the interior of the body member.

A space 231 is provided between the body member distal end 242 and the bridge portion 233 of end wall 230. A drainage tube 224 projects from the body member distal end 242 through a vertical bracket 296 attached to the lower or bottom end wall 272. The tubing 224 then projects through the adjacent flexible side wall 274 and terminates in a one-way valve 298 (not shown in detail) communicating with the interior 276 of the evacuation device 228. The one-way check valve 298 is identical to the one-way valve 98 described above with respect to the evacuation device 28 for permitting one way flow of urine only from tube 224 into the interior 276 of device 228. A conventional tubing clamp 322 is disposed over the drainage tube 224 between the sheath distal end 242 and the bracket 296 for clamping the drainage tube 224 closed as described above for the first embodiment. An air equalization tube 226 also projects from the distal end 242 of the body member 240, forms a "T" and branches into a pair of air equalization tubes 225 and 227. The pair of air equalization tubes 225 and 227 lay along the upper surface of the lower end wall 272 within the "U-shaped" space 229 and project toward the proximal end 244 of the sheath-like member 220, and then project transversely into the interior 276 of the device 228 through the flexible side walls 274 as shown in FIGS. 10 and 11A-11B at 291 and 293, respectively. The entry location 291 and 293 of the pair of air equalization tubes 225 and 227, respectively, are located to the "posterior" end of the evacuation device 228 in order that the communication of the tubes 225 and 227 will be "higher" than the vertical urine level 311 when the device is worn as shown in FIG. 9 for the reasons above described with respect to the location of the nipple 94 for tube 26 in the first embodiment of the evacuation device 28. In addition, each tube 225 and 227 have disposed therein a one-way check valve 270 to permit only one-way flow of air from the interior 276 of the evacuation device 228 in the same manner as valve 70 functions in tube 26 as above described. A tube clamp 312 is attached to the projecting tube 226 for clamping the air equalization tube closed in the same manner as the clamp 112 as above described with reference to embodiment 20 of the system. In FIG. 12, the air equalization tubes 226, clamp 312 and the branched pair of tubes 225 and 227 are not shown to simplify the drawing.

FIG. 11A shows the second embodiment of the evacuation device 228 in its fully expanded position, with the top end member 230 projecting near the upper level of the penile sheath body member 240, and corresponding to the expanded positions of the first embodiment of the evacuation device 28 (28') as shown in FIGS. 7A and 7B. Referring to FIGS. 10 and 11B, if the plug 302 (see FIG. 12) attached to the strap 304 is removed from nipple 300 and with the clamp 312 closed, pressure applied downwardly on top end 230 will expel air from the interior 276 of the device through the open nipple 300 and activate the evacuation device 228 as shown in FIG. 11B in the some manner as hereinabove described for the first embodiment as shown in FIG. 8. If the nipple 300 is plugged by plug 302 in the same manner that nipple 100 is plugged by plug 102 for the above-described evacuation device 28, and the pressure an end wall 230 is released, the evacuation device 228 will be activated. The springs 292 are biasing end wall 230 outwardly, thus exerting a negative pressure within the interior 276 of the device in the same manner as hereinabove described for the first embodiment 28.

As described above, the evacuation devices 28 and 228 are identical in function although differing in structure. Accordingly, in the description that follows, the function of the system 20 and 200 and the evacuation devices 28 and 228 will be described with respect to the first embodiment of the system 20 and the evacuation device 28, but it will be apparent that the functions described are identical in application to the second embodiment of the system 200 and the device 228 and that the described functions also describe the functions of the system 200 and the device 28.

In FIG. 13, the evacuator device 28 is shown in its energized position with the drainage tube 24 and air equalization tube 26 interconnecting the sheath member 22 and the evacuation device interior 76 through nipples 94 and 96, respectively, as above described. While the following description and discussion will be made with reference to the embodiment 28 of the evacuation device, the functions and general structural elements of the other embodiment 228 is nearly always identical thereto, and, accordingly, the description is equally applicable to both evacuation device embodiments 28 and 228. The plug 102 has been replaced within the nipple 100 for sealing the interior of the device 28. In order to prevent air from being forced upwardly through tubing 26 in the direction 108 shown in FIG. 8, in practice, when the evacuator device 28 is activated, it will be useful to close tubing 26, either by pinching the tubing by hand while the evacuator device 28 is being energized or by using a conventional tubing clamp 112 to block tube 26. The clamp 112 has a rotatable head 114 for driving a screw-actuated plunger 116 that will pinch closed the tubing as shown at 120. In addition, when the evacuator device 28 is energized as above described, it will be necessary to also close tubing 24, either by pinching the tubing by hand while the evacuator device is being energized or by using a conventional tubing clamp 122 that will pinch closed the tubing as shown at 130.

If the drainage tube 24 is not closed as above described, when the walls 30 and 72 of the evacuator device are released, the positive differential air pressure, acting through the body member 40 and tube 24, and applied to the one-way valve 98, would open the valve and allow positive atmospheric pressure into the interior 76 of the device 28, and thus cause the device to lose its negative pressure. The clamp 122 may be identical in construction to clamp 112, having a rotatable head 124 for actuating a screw-threaded plunger 126 that will pinch and collapse the walls of tubing 24 is shown at 130. Of course, clamps 112 and 122 may conveniently be any other clamping device or means that can function to close the tubes 24 and 26 as above described.

After the penis 65 is inserted into sealing contact with the interior 49 of body member 40 and the clamp 112 is opened, the negative pressure of the evacuator device 28 will be applied into the body member interior volume 49 to elongate the penis 65 into a pseudo erection as hereinabove described. Once the sealing member 50 operates to seal about the penile shaft 69, the clamp 122 may be opened for permitting fluid communication between the body member 40 and the evacuator device 28 through tubing 24. By closing tube 26 while the evacuation device 28 is being energized, maximum air within the interior 76 of the device 28 is expelled through the nipple 100 to achieve maximum suction or negative pressure therein. As shown in FIG. 13, a second one-way check valve 70' may be located in tubing 26 adjacent the end sealed in nipple 94.

Figure 14A:
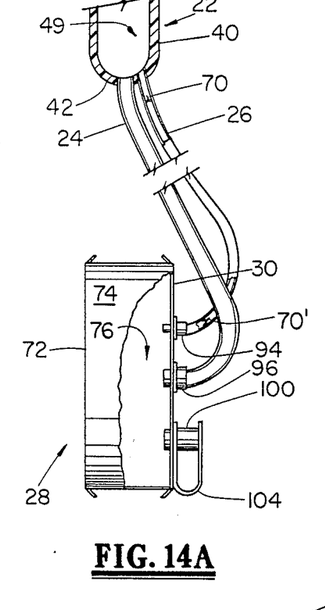
FIGS. 14A–14E are perspective views of a portion of the external male urinary catheter and collection system with the evacuation device partially cut-away for illustrating the sequence of events in energizing the negative pressure evacuation device, drainage and collection of urine, and the equalization of air pressure within the system.

The sequence of events from energizing the evacuation device, obtaining a simulated or pseudo erection and extension of the penis 65 within the body member 49 of the sheath-like member 22, through the urine collection and air equalization steps are shown sequentially in FIGS. 14A-14E. In FIG. 14A, a portion of the distal end 42 of the body member 40 is shown with its interior cylindrical inner space 49, interconnected to the evacuation device 28 by means of drainage tube 24 and the air equalization tube 26, as hereinabove previously described. As shown in FIG. 14A, the evacuation device 28 is not energized, and the springs 92 (see FIGS. 6-8, 11A and 12) would be fully expanded for holding the walls 30 and 72 in their maximum expanded position (The springs 92 have been deleted from FIGS. 14A-14E for simplification).

The next step (see FIG. 14B) is to energize the evacuation device 28 such as when the wearer is preparing to insert the penis 65 as previously described above with respect to FIGS. 2-5. By closing the drainage and air equalization tubes 24 and 26, either by manually pinching them shut with the fingers or, preferably by use of clamps 122 and 112, respectively, and then removing the plug 102 from nipple 100, the side walls 30 and 72 may be squeezed in the direction of the heavy arrows to compress the springs (not shown) and exhaust the maximum amount of air from interior space 76 through the discharge nipple 100 as shown by the arrow 110.

Figure 14B:
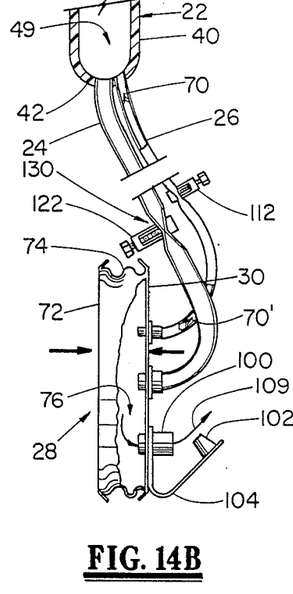
Figure 14C:
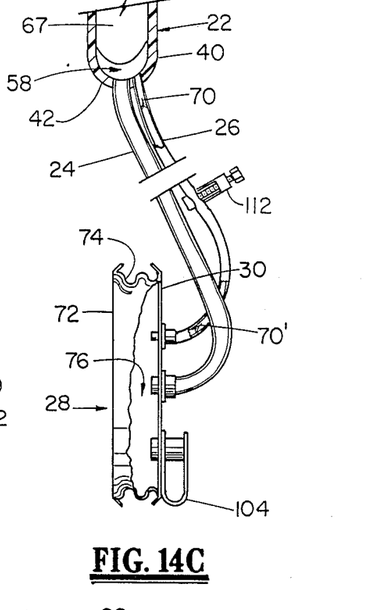

As shown in FIG. 14C, by replacing the plug 102 into the nipple 100, releasing the pressure on the evacuation device side walls 30 and 72, and opening the tube clamp 122 on tube 24, the negative pressure within the interior 76 of device 28 will be communicated through the drainage tubing 24 from the interior 49 of the body member 40 and thus apply a negative pressure within the body member interior 49 for acting on the flaccid penis 65 (see FIGS. 3-5). As previously described, the negative pressure therein will cause the penis to expand and lengthen to its anatomical limit until it either fills the body member interior 49 or substantially fills the body member interior 49 leaving only a relatively small potential space 58 between the end of the glans penis 67 and the interior rounded surface of the distal end 42 of member 40 (see FIGS. 4 and 5). The clamp 112 on the air equalization tube 26 may then be removed. In most circumstances, if the tubing 26 is of a relatively thin-wall flexible type, the tubing will probably collapse at 120 after the clamp 112 is opened due to the negative pressure therein, effectively continuing to seal off the tubing 26. With the penis 65 completely extended within the body member 40, and with the evacuation device 28 attached to the wearer's leg (see FIG. 1) the evacuation device 28 will be oriented in the vertical position as shown. Accordingly, the external male urinary catheter and collection system is now ready for collecting urine passed by the wearer.

Figure 14D:
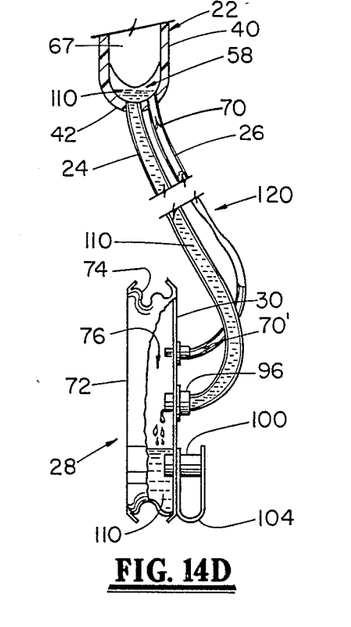

Referring now to FIG. 14D, when the incontinent wearer passes urine into the interior of the body member 40, because the positive pressure of the expelled urine within the body member interior 49 is greater than the negative pressure within the interior 76 of the evacuation device 28, the urine will readily flow through the drainage tube 24 and the one-way check valve 98 (see FIG. 7) and then into the evacuation device interior volume 76 for collection as shown at 110. As the urine passes into the body member 40, it will tend to fill the drainage tube 24 and may collect within the potential space 58, if the space is available, between the end 68' of the glans penis 67 and the inner distal body member end 43. The volume of urine passed by the wearer will continue to pass through the drainage tube 24 into the interior 76 of device 28, until the volume of urine entering the interior space 76 displaces a sufficient quantity of air within space 76 to "raise" the negative pressure to a more positive value and apply a "positive" differential pressure across the check valves 70 and/or 70' disposed within tubing 26.

Such a positive differential pressure across the valves 70 and/or 70' will permit a predetermined volume of air, functionally related to the volume of air displaced by the volume of urine 110 discharged into the evacuator device interior 76, to flow directly into the inner volume of the body member 40. This "equalization flow" of air through tubing 26 in the direction 108 will be sufficient to force open the tubing 26 at 120 and allow the volume of air to flow into the interior of body member 40 and thus provide a volume of air to displace any urine 110 that may remain pooled in any available space 58 in the distal end 42 of the body member 40 or in the tube 24. The more "positive" air pressure within the body member 40 will cause a volume of urine 110 to be expelled from the drainage tube 24 into the interior 76 of device 28, thus lowering the urine 110 level within the drainage tube 24 to some intermediate level 132 (see FIG. 14E).

Figure 14E:
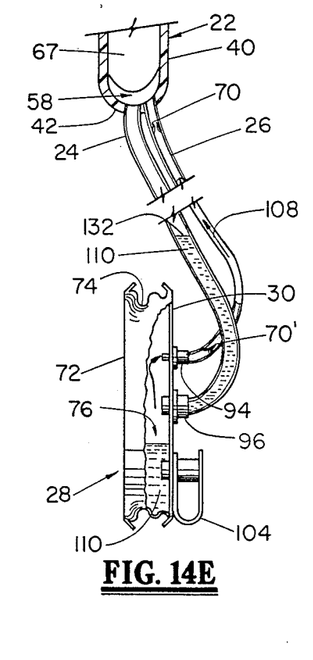

This lowering of the level o urine 110 within the drainage tube 24 to an intermediate level 132 eliminates the possibility of pooling of urine within any potential space 58 in the distal end 42 of the body member 40. The elimination of urine within a possible space 58 eliminates the presence of the urine in contact with the glans penis 67, thus overcoming and eliminating any possibility of skin irritations and infections. The volume of air that flows through the equalization tube 26 into any space 58 or the interior of body member 40 tends to equalize the negative pressure within the system, as created by the energized evacuation device 28, and establish pressure equilibrium within the system. That equilibrium will continue until additional urine is discharged into the body member 40 as shown in FIG. 14D, and a corresponding air equalization has taken place as shown in FIG. 14E. The cycling between steps as shown in FIGS. 14D and 14E will continue until such time as the evacuation device 28 has collected a maximum amount of urine 110.

The air pressure within the body member 40 and/or tube 24 can also be raised by manually compressing walls 30 and 72 (as shown above in FIG. 14B). Such compression will drive the remaining air within device 28 through the air equalization tube 26 and valve 70 and/or 70' into the interior of body member 40. Such a displacement of air through tube 26 will raise the air pressure within body member 40 forward of the penis end 68 for displacing a volume of urine from tube 24 and, potential space 58 to lower the urine level to the level as shown at 132 in FIG. 14E.

To empty the evacuation device 28, the clamps 112 and 122 attached to tubes 24 and 26 may both be closed and the plug 102 removed from nipple 100 for permitting drainage of the urine therethrough. The interior 76 of device 28 will go to normal atmospheric pressure and the evacuation device 28 will expand to its original expanded shape as shown in FIG. 14A. However, since the tubes 24 and 26 have been clamped shut, and the higher pressure within the interior space 76 cannot pass through the check valves 96 and 98 (not shown) into tubing 24, the negative pressure within the body member 40 is maintained and the negative pressure seal is maintained by the sealing member 50. Additional negative pressure may be applied by activating device 28 as previously described and opening clamps 112 and 122.

The interior 76 of the evacuation member 28 may be suitably washed or cleaned by injecting appropriate cleansing solutions through the open nipple 100, and then the evacuation device 28 can be reactivated as shown in FIG. 14B for continuation through the sequence of steps as shown in FIGS. 14C, 14D and 14E as hereinabove described.

Numerous variations and modifications may be made in the structure herein described without departing from the present invention. Accordingly, it should be clearly understood that the forms of the invention herein described and shown in the figures of the accompanying drawings are illustrative only and are not intended to limit the scope of the invention.

I claim:

1. An external male urinary catheter and collection system, comprising
    a generally tubular hollow body member having a distal closed end and a proximal open end for accommodating a portion of the male penis interiorly thereof,
    a flexible thin-walled sleeve-like sealing member integrally extending from said proximal open end of said body member and oriented in concentric axial alignment therewith,
    said sleeve-like sealing member having a wall thickness substantially less than the wall thickness of said body member and adopted to be rolled up over the open end of the adjacent portion of said body member to permit insertion of the distal end of the male penis therein,
    said sleeve-like sealing member having a predetermined substantially constant inner circumferential dimension selected for permitting said sealing member to snugly contact the exterior surface of the non-erect penile shaft when returned to the unrolled extended position,
    ambulatory evacuation means that is self-contained and independently operable for producing a negative pressure therein and capable of receiving and collecting urine interiorly thereof,
    a drainage tube interconnecting the distal end of said body member and said evacuation means for providing fluid communication therebetween and permitting drainage of urine from said body member interior to said evacuation means for collection,
    first one-way valve means cooperating with said drainage tube for permitting fluid flow through said drainage tube only in the direction from said body member to said evacuation means,
    said negative pressure from said evacuation means being communicated through said drainage tube and first one-way valve means into the interior of said body member for cooperating with the inserted male penis for permitting it to expand to its anatomic limit in a simulation of an erection into the interior of said body member, said negative pressure introduced within said body member further acting on said thin-walled sleeve-like sealing member for collapsing said thin walls about a non-erect portion of the penile shaft and maintaining an air-tight seal therewith but not engaging the non-erect penile shaft tightly enough to restrict venous blood flow therein,
    a second tube interconnecting the distal end of said body member and said evacuation means and said second tube communicating with said drainage tube through the interior of said body member,
    a second one-way valve means cooperating with said second tube for permitting air flow therethrough only in the direction from said evacuation means to said body member, and wherein said second tube and second one-way valve means cooperate with said evacuation means and body member for permitting an intermittent displacement of air therethrough from said evacuation means into said body member interior in response to the intermittent drainage of urine into said evacuation means through said drainage tube and first one-way valve means, and displacing sufficient urine in said drainage tube into said evacuation means for insuring that substantially no urine remains interiorly of said body member distal end.

2. The apparatus as described in claim 1, wherein the junction of said integrally extending sleeve-like sealing member with said proximal end of said body member includes an annularly radiused shoulder having a variable cross-sectional thickness tapering from a thin-walled end integral with said sleeve-like sealing member to a thicker-walled end integral with the proximal end of said body member.

3. The apparatus as described in 1, wherein said ambulatory evacuation means comprises a container of flexible material, said container being resiliently compressible when subjected to manual pressure and upon release of said manual pressure being resiliently expansible to create a negative pressure therein.

4. The apparatus as described in claim 3, wherein said resiliently compressible container is provided with a drain opening and a closure plug for closing said opening, said drain opening permitting exhaustion of air from the interior of said container when said container is manually compressed and drainage of urine from the interior of said container.

5. The apparatus as described in claim 3, wherein said drainage tube has flexible walls and further includes a first closure means cooperating therewith to selectively close said tube and prohibit fluid flow therethrough when said container has been manually compressed for prohibiting air flow through said drainage tube from said body member prior to insertion of the penis into sealing contact with said sealing member.

6. The apparatus as described in claim 5, wherein said first closure means comprises a tubing clamp externally cooperating with said flexible walls of said drainage tube for manually clamping shut said drainage tube.

7. The apparatus as describe in claim 3, wherein said second tube has flexible walls and further includes a second closure means cooperating therewith to selectively close said tube and prohibit air flow therethrough when said container is manually compressed.

8. The apparatus as described in claim 7, wherein said closure means comprises a clamp externally cooperating with said flexible walls of said second tube for manually clamping shut said second tube.

9. The apparatus as described in claim 8, wherein release of said clamp from said second tube permits the intermittent displacement of air therethrough in a volume functionally related to the volume of air displaced interiorly of said container by the intermittent drainage of urine into said container.

10. The apparatus as described in claim 3, wherein said second tube interconnects to said flexible container at a location that will remain above the maximum level of urine collected in said container.

11. The apparatus as described in claim 3, wherein said container further includes a strap for attaching said container to the wearer's leg.

12. The apparatus as described in claim 3, wherein said resiliently compressible container has at least one curved end wall for contacting and conforming to the curvature of the wearer's leg, and further includes a strap for attaching said container to the leg.

13. The apparatus as described in claim 3, wherein said resiliently compressible container has an elongated opening disposed therein for accommodating a longitudinal distal portion of said body member, said container being attached to said body member for functioning as a unitary assembly.

14. The apparatus as described in claim 13, wherein said resiliently compressible container has at least one curved end wall for contacting and conforming to the curvature of the wearer's leg, and further includes a strap for attaching said container to the leg.

15. The apparatus as described in claim 13, wherein said container further includes a strap for attaching said container to the wearer's leg.

16. The apparatus as described in claim 1, wherein said first and second one-way valve means comprise first and second one-way check valves.

17. The apparatus as described in claim 16, wherein said second one-way check valve comprises a one-way duck-bill valve.

18. An external male urinary catheter and collection system, comprising
a generally flexible tubular hollow body member having a distal closed end and a proximal open end for accommodating a portion of the male penis interiorly thereof,
a flexible thin-walled sleeve-like sealing member integrally extending from said proximal open end of said body member and in concentric axial alignment therewith,
a drainage tube one end of which is connected to the distal end of said body member for fluid communication therewith,
first one-way valve means cooperating with said drainage tube to permit one-way fluid flow therethrough from said body member interior,
an air tube one end of which is connected to the distal end of said body member adjacent said drainage tube for fluid communication with the interior of said body member and with said drainage tube,
second one-way valve means cooperating with said air tube to permit one-way fluid flow therethrough into said body member interior, and
portable evacuation means interconnected to the other ends of said drainage and air tubes for communicating therethrough to the interior of said body member, said evacuation means being self-contained and independently operable for producing a negative pressure therein and receiving and collecting urine therein,
said sleeve-like sealing member having thin-walls for permitting said sealing member to be rolled up over the adjacent portion of said body member to permit the insertion of the distal end of the male penis into the proximal end of said body member and then allowing said sleeve-like sealing member to be returned to its unrolled extended position in snug circumferential contact with the exterior of a portion of the nonerect penile shaft,
wherein said negative pressure introduced into said body member interior acts on the non-erect penile shaft for drawing the penis into the interior of said body member to near its anatomical limit in a simulation of an erection, and further acting on said thin-walled sleeve-like sealing member for collapsing said thin walls about the penile shaft in circumferential contact therewith for maintaining an airtight seal therebetween, and wherein said air tube and said second one-way valve means cooperate with said evacuation means and body member for permitting an intermittent displacement of air therethrough from said evacuation means into said body member interior in response to the intermittent drainage of urine into said evacuation means and displacing sufficient urine in said drainage tube into said evacuation means for insuring that substantially no urine remains interiorly of said body member distal end.

19. The apparatus as described in claim 18, wherein the junction of said integrally extending sleeve-like sealing member with said proximal end of said body member includes an annularly radiused shoulder having a variable cross-sectional thickness tapering from a thin-walled end integral with said sleeve-like sealing member to a thicker-walled end integral with the proximal end of said body member.

20. The apparatus as described in claim 18, wherein said evacuation means is a self-contained independently operable device for ambulatory use and comprises a container of flexible material, said container being resiliently compressible when subjected to manual pressure and upon release of said manual pressure being resiliently expansible to create a negative pressure therein.

21. The apparatus as described in claim 20, wherein said resiliently compressible container is provided with a drain opening and a closure plug for closing said opening, said drain opening permitting exhaustion of air from the interior of said container when said container is manually compressed and drainage of urine from the interior of said container.

22. The apparatus as described in claim 20, wherein said drainage tube has flexible walls and further includes a first closure means cooperating therewith to selectively close said tube and prohibit fluid flow therethrough when said container has been manually compressed for prohibiting air flow through said drainage tube from said body member prior to insertion of the penis into sealing contact with said sealing member.

23. The apparatus as described in claim 22, wherein said first closure means comprises a tubing clamp externally cooperating with said flexible walls of said drainage tube for manually clamping shut said drainage tube.

24. The apparatus as describe in claim 22, wherein said second tube has flexible walls and further includes a second closure means cooperating therewith to selectively close said tube and prohibit air flow therethrough when said container is manually compressed.

25. The apparatus as described in claim 24, wherein said second closure means comprises a tubing clamp externally cooperating with said air tube flexible walls for manually clamping shut said air tube.

26. The apparatus as described in claim 25, wherein release of said clamp from said air tube permits the intermittent displacement of air therethrough in a volume functionally related to the volume of air displaced interiorly of said container by the intermittent drainage of urine into said container.

27. The apparatus as described in claim 20, wherein said air tube interconnects to said flexible container at a location that will remain above the maximum level of urine collected in said container.

28. The apparatus as described in claim 27, wherein said container further includes a strap for attaching said container to the wearer's leg.

29. The apparatus as described in claim 20, wherein said resiliently compressible container has at least one curved end wall for contacting and conforming to the curvature of the wearer's leg, and further includes a strap for attaching said container to the leg.

30. The apparatus as described in claim 20, wherein said resiliently compressible container has an elongated opening disposed therein for accommodating a longitudinal distal portion of said body member, said container being attached to said body member for functioning as a unitary assembly.

31. The apparatus as described in claim 30, wherein said resiliently compressible container has at least one curved end wall for contacting and conforming to the curvature of the wearer's leg, and further includes a strap for attaching said container to the leg.

32. The apparatus as described in claim 30, wherein said container further includes a strap for attaching said container to the wearer's leg.

33. The apparatus as described in claim 18, wherein said first and second one-way valve means comprise first and second one-way check valves.

34. The apparatus as described in claim 33, wherein said second one-way check valve comprises a one-way duck-bill valve.

* * * * *